United States Patent [19]

Lozar

[11] Patent Number: 4,583,854

[45] Date of Patent: Apr. 22, 1986

[54] HIGH RESOLUTION ELECTRONIC AUTOMATIC IMAGING AND INSPECTING SYSTEM

[75] Inventor: Boris Lozar, Milan, Italy

[73] Assignee: General Electric Company, Detroit, Mich.

[21] Appl. No.: 513,486

[22] Filed: Jul. 13, 1983

[30] Foreign Application Priority Data

Jul. 15, 1982 [IT] Italy .................................. 22401 A/82
Mar. 20, 1983 [IT] Italy .................................. 19860 A/83

[51] Int. Cl.⁴ ............................................ G01N 21/88
[52] U.S. Cl. ..................................... 356/237; 356/69; 250/224
[58] Field of Search ......................... 356/237, 69, 445; 73/104; 250/224; 350/523, 612, 618, 622

[56] References Cited

U.S. PATENT DOCUMENTS

| | | | |
|---|---|---|---|
| 2,027,595 | 1/1936 | Knobel et al. | 356/69 |
| 3,025,747 | 3/1962 | Casselman et al. | 356/69 |
| 3,240,112 | 3/1966 | Erban | 356/69 |
| 4,162,126 | 7/1979 | Nakagawa et al. | 356/237 |

Primary Examiner—John Kittle
Assistant Examiner—Thomas C. Saitta
Attorney, Agent, or Firm—A. E. Bahr; E. F. Chapman; J. J. Lichiello

[57] ABSTRACT

In a high resolution optical electronic imaging system to detect defects and dimensional changes in articles of manufacture for example, metal cutting tool inserts, a convergent blade-shaped laser light beam emitted by a laser passes through a focusing optical system and is then directed to a revolving head which contains a mirror system. The focusing and mirror system scans the apex of the blade beam along the cutting edges of an insert so that edge defects and dimensional changes cause reflection and refraction of the laser beam. High resolution and contrast television camera and optic system receives the reflections and refractions and creates an image of the device with sharply contrasted defects.

15 Claims, 11 Drawing Figures

HIGH RESOLUTION ELECTRONIC AUTOMATIC IMAGING AND INSPECTING SYSTEM

BACKGROUND OF THE INVENTION

This invention relates to an imaging system for obtaining a high resolution optical-electronic image of test pieces or bodies generally and, particularly, for producing a high resolution image capable of distinguishing relatively small details, such as defects and dimensional changes in hard metal inserts used for machining operations, i.e. turning, milling, planing and the like.

This invention is in particular applicable to the inspection of the cutting-edges of hard metal inserts in order to detect defects, such as chippings, on said cutting edges and dimensional variations, and to automatically select or classify said inserts.

Particular problems encountered during the production of hard metal inserts are dimensional inspection, detection of defects on the cutting edges, and qualitative classification according to size tolerances and the number of defects detected on the cutting edges.

It is an object of this invention to provide an improved automatic inspection system having the above described properties. In order to automate insert inspection, this invention uses a type of optical-electronic system which translates optical images into electric signals. The system can detect defects of different types by adjusting its resolution power.

SUMMARY OF THE INVENTION

A unique method of to distinguishing defects in the range of a tenth of a millimeter on the cutting edges of inserts, comprises illuminating the cutting edges of said inserts with a laser beam while the inserts are resting on a plane in a dark background. The illumination is in the form of a blade-shaped light beam which has a minimum width, and therefore maximum intensity at an area coinciding with the cutting edge to be inspected. Means are provided for relative motion between the said blade-shaped beam and the edge of the insert. Each individual deformation of the edge will result in a perturbating source for the blade-shaped beam which, due to the concentration of luminous energy at the point of its correspondence with the edge, will create an easily detectable light contrast, against the remaining portion of the edge, which can be detected and recorded by optical-electronic systems.

In one embodiment of this invention, the blade-shaped beam is obtained by using a laser as light source, and by passing the light so produced through suitable optical equipment which is provided with a cylindrical lens to form the blade-shaped beam useful for this invention. A revolving head, containing one or more mirrors, enables the blade-shaped beam to be moved along the side surface or edge of the insert to be inspected, while an optical-electronic detector, for example a television (TV) camera equipped with a VIDICON tube, will translate an image of the insert edges with its defects into electric signals. These signals can be used to represent the insert edges on a television monitor, giving an image of said edges which will particularly outline or define the defect areas.

The signals from the camera can also be delivered to an electronic processor which will check the insert size and detect and record the defects on the edges of said inserts. The processor will also classify and select inserts according to the number of defects as detected for each individual insert. This classification is useful for rejecting defective inserts and for packaging the inserts according to quality groups, i.e. groups having dimensional tolerances and number of defects falling within selected intervals. In such a manner, a complete inspection or checking of the produced inserts, and a distribution of the same to quality groups, are obtained.

Also, a suitable focusing system is combined with the optical system which is moveable in such a way that the distance between the optical system and a polygon insert edge remains unchanged, independently of the insert size and configuration.

THE DRAWINGS

This invention will be better understood from the following description of some embodiments in conjunction with the accompanying drawings, wherein.

DISCUSSION OF PREFERRED EMBODIMENTS

Figure 1:
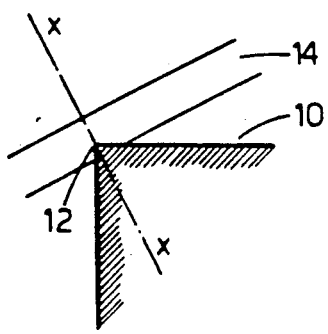
FIG. 1 shows the corner edge of a hard metal insert illuminated by a blade-shaped light beam according to the imaging system of this invention.
Figure 2:
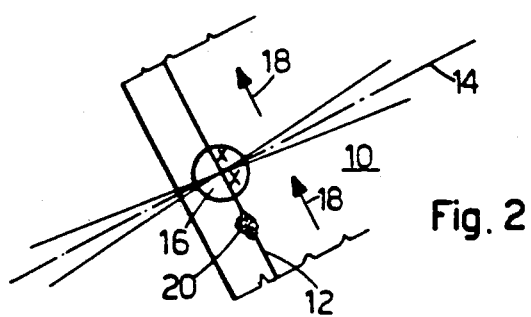
FIG. 2 shows a three dimensional plan view of the insert of FIG. 1 under similar inspection.

Referring now to FIGS. 1 and 2, it can be observed that for defect detection on a hard metal insert 10, provided with cutting edge 12, the insert is held in a dark background and a blade-shaped light beam 14 is used, which has a minimum width on an axis X—X perpendicular to the propagation direction of same beam and located within a region 16, FIG. 2, centered on said cutting edge 12. Beam 14 is moved in a direction indicated by arrows 18, parallel to the cutting edge 12 and then it is diffracted or scattered by said edge 12 according to known optical laws. A defect on the edge, such as a chip 20, will form a substantial deviation from the geometrical form of the cutting edge 12 which will cause a substantial variation of the diffraction phenomena of the ray 14 by said edge 12. Owing to the concentration of light energy along the axis X—X, this variation of the diffraction phenomena will produce an easily detectable light contrast on the insert dark bottom. A photo, taken of the insert illuminated by the light beam 14 sliding on a cutting edge 12, represents the image of the cutting edge from which the defects are contrasted.

Figure 3:
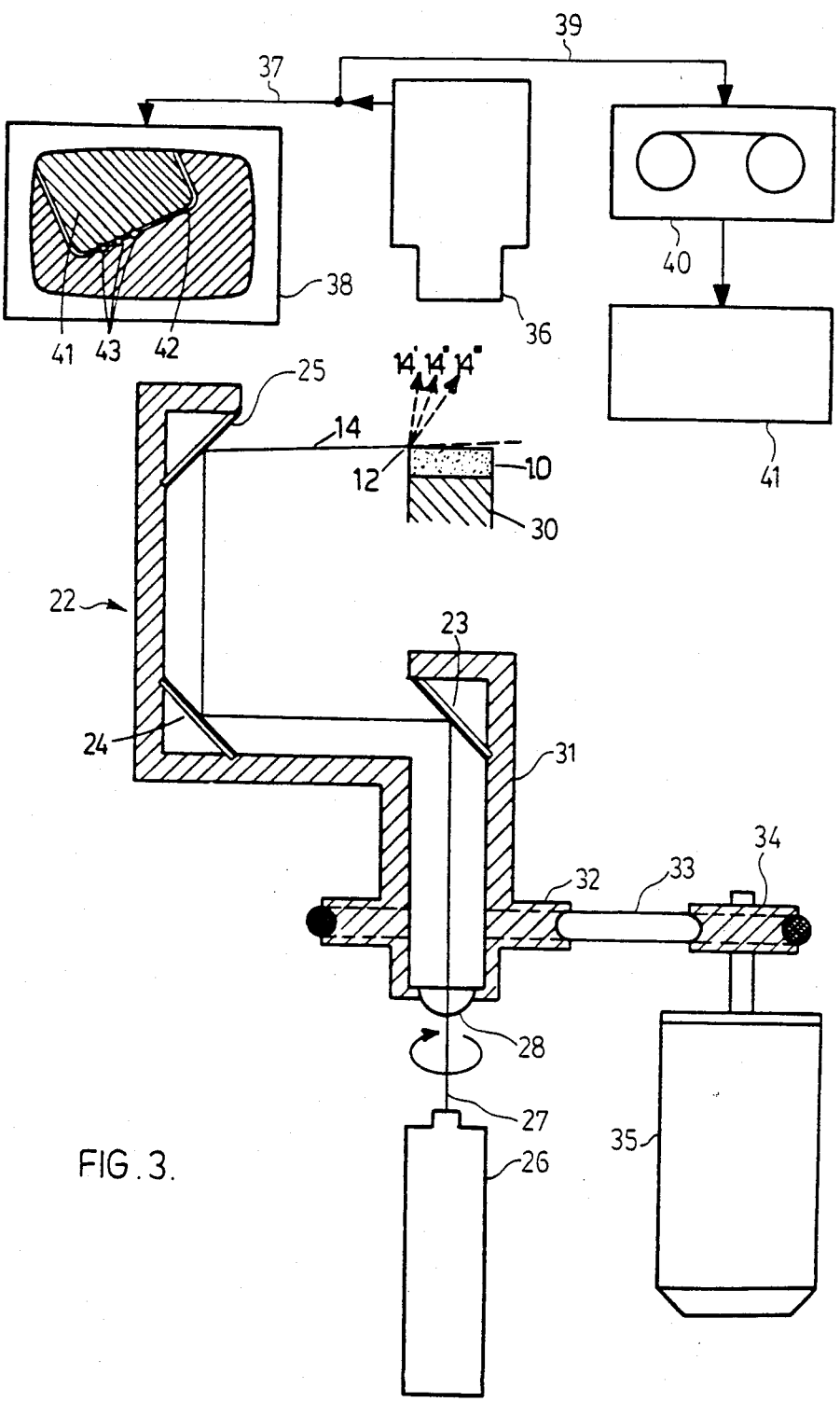
FIG. 3 shows a first apparatus for embodying this invention.

A first embodiment of this invention is illustrated in FIG. 3 showing an optical system or group 21 used to inspect an insert by means of a grazing and sliding light beam 14 over a cutting edge 12 of the insert. In particular, the optical system employs a revolving head 22 containing three mirrors 23, 24 and 25 which are arranged to reflect a light beam at 90° with respect to each other and to pass along an axis passing along the insert with a slight angle of incidence, i.e. in a grazing and sliding way along the edge of the insert which is to be illuminated. In optical system 21 a light source, such as a laser 26, emits a light beam 27 which is shaped as a blade by means of a cylindrical lens 28, being a part of the optical system connected to source 26. The shaped beam 14 coming from the cylindrical lens 28 enters revolving head 22 the purpose of which is to move a light beam 14 coming from said revolving head 22 over a cutting edge 12 of an insert 10 which is fastened to a fixed support 30.

The revolving head 22 comprises a hollow sleeve or spindle 31 through which passes the beam 27 to impinge on a first mirror 23 which along with additional mirrors 24 and 25 will coact to reflect said beam as a beam 14 sliding and grazing along the cutting edge 12 of the insert 10. The rotary movement of the revolving head 22 is provided by a pulley 32 connected through a belt 33 to another pulley 34 keyed onto the shaft of an electric motor 35.

The light beam 14 is scattered by the cutting edge 12 and by its defects, according to the known laws of light diffraction, giving some diffracted or scattered beams 14', 14'', 14''', . . . The diffracted beams are detected by an image detector 36, for example a TV camera. The signals coming from camera 36 are delivered through a first line 37 to a television monitor 38 and then through a second line 39 to an electronic processing unit 40, which executes the dimensional checking and the counting of the defects on the cutting edges of the inserts, as well as classification of the inserts according to tolerances. Some additional apparatus 41, not being a part of this invention, can be used for proper packaging of the classified inserts. The monitor screen 38 shows an image 41 of the insert wherein the image 42 of the cutting edge and the images 43 of the defects, such as chippings, on said cutting edge are specifically marked.

Figure 4:
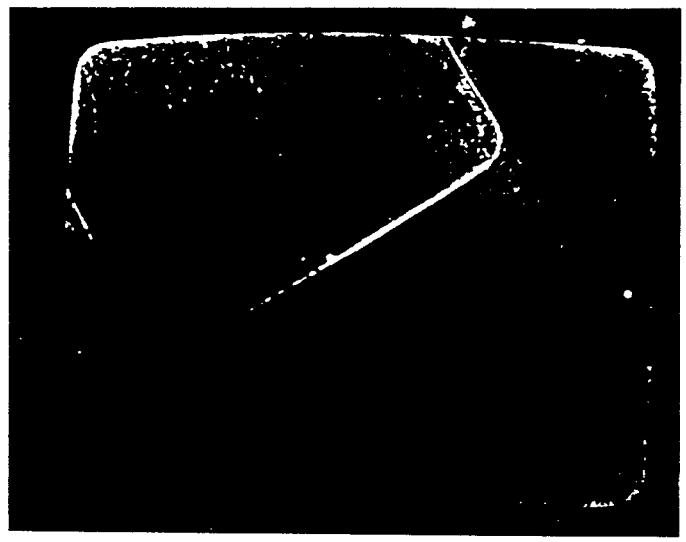
FIG. 4 is a photo of an image of a cutting edge of inserts taken by the use of the imaging system of this invention.
Figure 5:
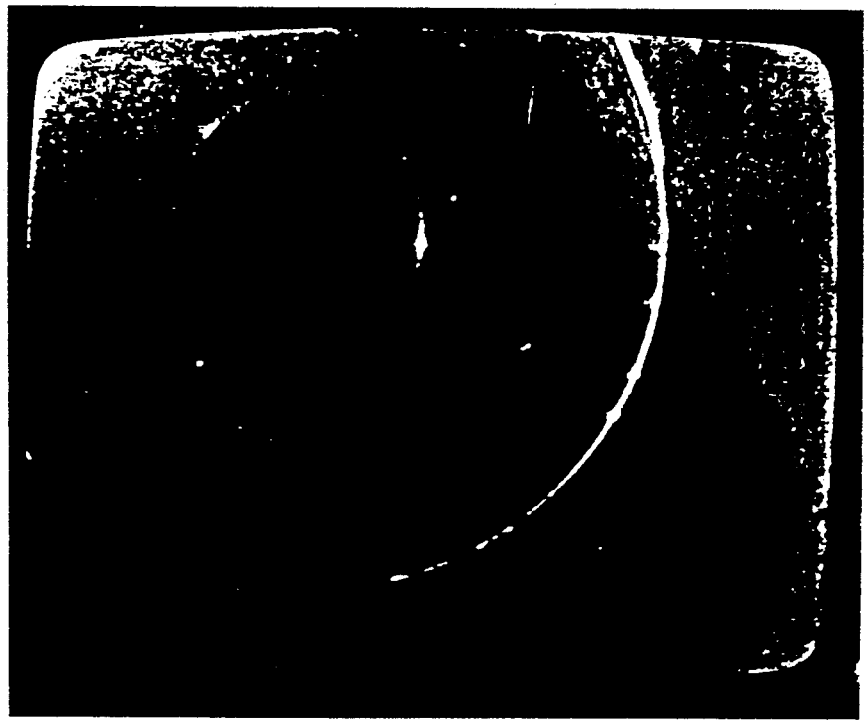
FIG. 5 is a similar photo of another insert.

FIGS. 4 and 5 are photographs of the images on the television monitor, respectively, concerning a square insert and a round insert, wherein the cutting edges of said inserts and their defects are particularly visible.

Figure 6:
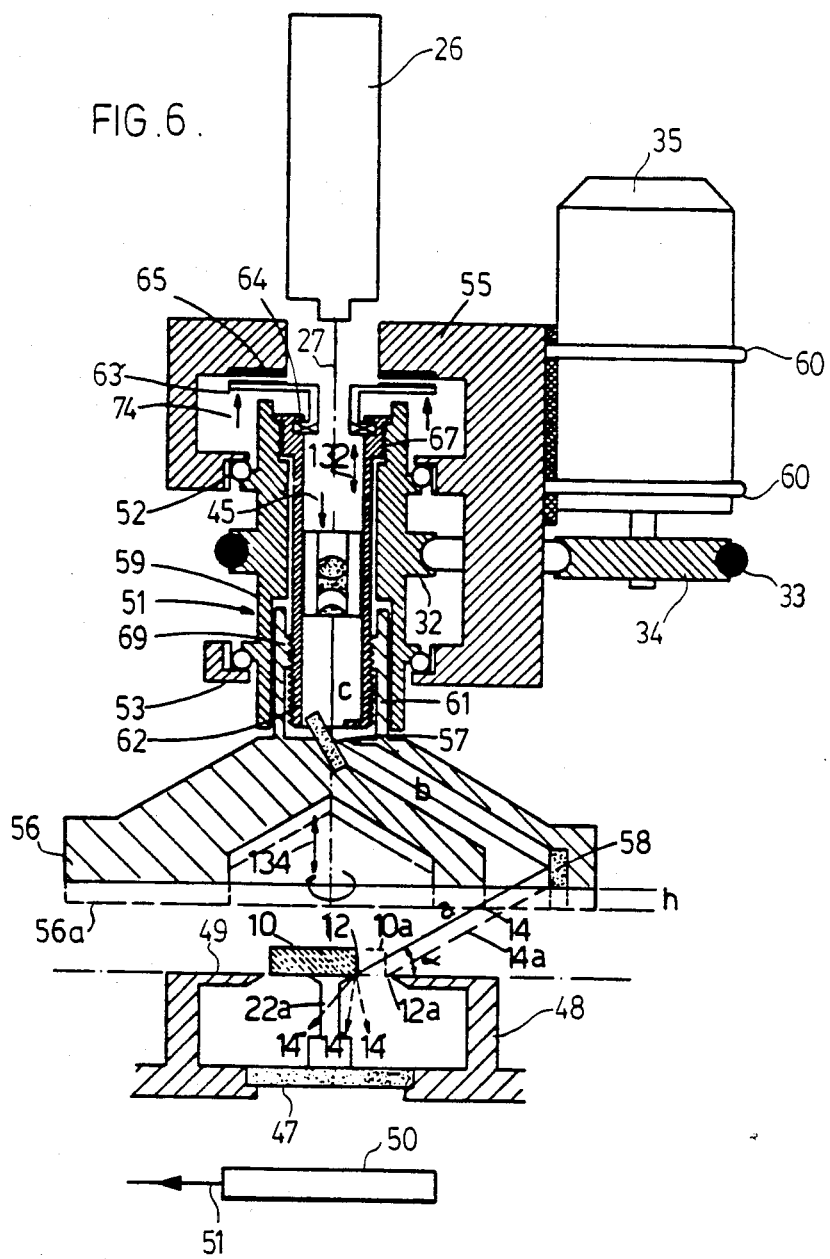
FIG. 6 shows a second apparatus for embodying this invention.

A second and preferred embodiment of this invention is illustrated in FIG. 6 which represents an improved apparatus 44 for the inspection of cutting edges of inserts by means of a sliding and grazing laser light beam. Apparatus 44 comprises a light source, such as a laser 26, which emits a light beam 27, passing through a system of lens in an optical group 45, containing also a cylindrical lens, to produce the blade-shaped beam 14 used for the sliding illumination or lighting of a cutting edge 12 of an insert 10 to be inspected. Insert 10 comprises a pair of substantially parallel side surfaces which are interconnected by a planar edge surface which defines a cutting edge 12 therewith. The insert 10 is supported by a support 46 which, in turn, is supported by a transparent plate 47, for example glass. Transparent plate 47 rests against a support 48, defining a reference plane 49 on which the cutting edge 12 of the insert 10 is positioned as illustrated. An image detector 50 is located under said transparent plate 47, to provide for dimensional stability of the images against temperature, and also isolation from mechanical vibrations. The image detector 50 is preferably of the solid state type (charge coupled image detector).

The optical system 45 is housed within a revolving assembly 51 mounted by means of two ball bearings 52 and 53 on a stationary support 55. A bell type head 56, revolving with the unit 51, bears two mirrors 57 and 58, one of which produces a reflection angle "90°+$\alpha$" and the second one a reflection angle "2$\alpha$". The reflected beam is properly inclined at an angle "$\alpha$" to the supporting plane of the insert, thus allowing an easy coincidence of the focus of the blade-shaped beam with the edges of said insert. In particular, by selecting $\alpha=30°$, reflection angles of 120° and 60° are obtained respectively. The purpose of mirrors 57 and 58 is to reflect the blade-shaped beam 27 for making it project as a sliding and grazing beam 29 on the cutting edge 12 of the insert 10. The light of said blade-shaped beam is diffracted, according to the defects detected on the cutting edges 12, into beams 14', 14'', 14'''. . . , which are collected by the image detector 50, which through a line 51 will send the corresponding electric signals to the connected equipment.

The revolving assembly 51 comprises a first outer sleeve or hollow spindle 59 equipped with a pulley 32 rotated by belt 33 engaging pulley 34 which is keyed to a shaft of an electric motor 35. Motor 35 is secured, by suitable means, such as the brackets 60, to the stationary support 55.

A second intermediate sleeve 61 integral with the bell shaped head 56 is internally and coaxially located within sleeve 59, while a third internal sleeve 62 is integral with the optical group 45 and usually is moved along with the other two sleeves. A disc brake 63, equipped with a central sleeve ending with a crown gear 64, presses against a pad 65, secured to the support 55, to stop internal sleeve 62 for the purposes hereafter illustrated. The internal sleeve 62 is equipped with one external upper thread 67 having a first pitch "f" and threading into a corresponding internal thread 68 of the outer sleeve 59, and a second outer lower thread 69 having a pitch "F" larger than the pitch "f", threaded into a corresponding internal thread 70 of the intermediate sleeve 61.

Figure 7:
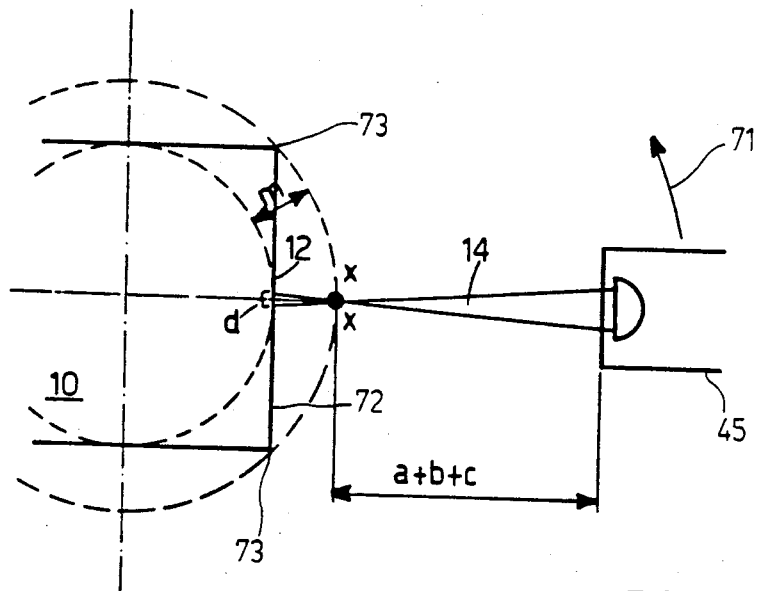
FIG. 7 illustrates in detail the principle for adapting the apparatus to the inspection of inserts of different sizes while maintaining, unchanged, the distance between the optical system centerline and the axis of the light beam of the FIG. 6 apparatus.

Referring now to FIG. 7, there is shown a plan and schematic view of a non-round insert 10 illuminated by a light blade 14 coming from an optical group 45. Due to the revolving motion of the mirrors 57 and 58, shown in FIG. 6, the optical group 45 operates as if it is revolving about the insert 10 according to the arrow 71. Consequently, the light blade 14 will scan all the cutting edges of the insert 10 and, owing to the non-round or polygon shape of the insert, the distance between the optical group 45 and the insert 10 will vary of a value "m" equal to the difference of the distance between the optical group 45 (a+b+c+m) and the center of the flat portion 72 of the cutting edge 12, and the distance between said optical group 45 and the corners 73 of said cutting edge 12. Accordingly, the light blade 14 when it encounters the cutting edge 12 has a thickness "d" varying along the flat portion 72 of the cutting edge 12 up to a minimum value at the corners 73. As the thickness "d" of the light blade becomes smaller, light intensity of the light blade 14 on the cutting edge 12 becomes proportionately higher and, therefore, the image resolution is greater. It is important that the location of axis X—X occur at the corners 73 of the cutting edges 12, since the probable chips on the edges 12 have a higher importance than those on the flat portions of the cutting edge 12, such as the portion 72.

Since inserts having different dimensions are to be inspected through this imaging system, it is necessary to operate in such a way that said location of the axis X—X will always occur on the corners 73 of the cutting edge 12, independently of the dimensions of the inspected insert.

In order to make the axis X—X always coinciding with the edges 12 of the inserts, it is necessary to change the focusing distance of the optical group 45, a problematic procedure, owing to the shape of the light ray 14, or to keep the focusing distance of the optical group 45 unchanged, move it with respect to the insert 10 for accounting of its dimensions. Naturally, owing to its simplicity the latter solution is preferred.

Referring now to both FIGS. 6 and 7, it can be observed that the focusing distance of the optical group 45 is given by the sum of distances a, b and c. When the insert 10 is replaced by an insert 10 of a larger dimension, the bell 56 should be lowered by a distance "h" (FIG. 6), bringing it to a position 56a, so that the blade-shaped beam (now 14a) will graze the cutting edge 12a of the new insert. However, since the blade-shaped beam 14 is inclined by an angle $\alpha$ with respect to the reference plane 49, the distance a will decrease by a value $h/\sin\alpha$. In order to maintain the focusing distance given by a+b+c unchanged, the distance c is increased by a value equal to $h/\sin\alpha$. This is obtained through the above mentioned system having three threaded and coaxial sleeves 59, 61 and 62.

In order to change the distance c and, at the same time to lower the bell 56, the disc brake 63 which is located internally of the revolving assembly 51 is utilized. By exerting a force according to the arrow 74 on the disc brake 63, it is engaged against pad 65 secured to stationary support 55, thus stopping the disc 63 and, accordingly, preventing the revolving of the internal sleeve 62 which is engaged with the crown gear 64 of the disc brake 63. Now, by slowly rotating, for example manually, the revolving unit 51, the internal sleeve 62 cannot rotate together with the outer sleeve 59 and, accordingly, owing to the upper threads 67 and 68, it will move axially in respect to it, for example upwardly. At the same time, the intermediate sleeve 61, which is engaged in rotation by the outer sleeve 59, owing to the lower threads 69 and 70, will move axially with respect to the internal sleeve 62 in opposite direction, for example downwardly. Since the thread 69 has a pitch "F" larger than that of the thread 67, the intermediate sleeve 61 is subject to a lifting motion due to the thread 62 and a lowering motion due to the thread 67, and it will be lowered for a distance porportional to "F-f", the pitch difference between the threads, while the intermediate sleeve 61 will move away from the internal sleeve 62 for a distance proportional to the pitch "F" of the thread 67. Therefore, in order to change the distance c of a portion equal to $h/\sin\alpha$, by changing the position of the bell 56 of a distance h, it is necessary that the upper thread 62 will rotate oppositely with respect to the lower thread 69, that the pitch "f" of the upper thread 67 and the pitch "F" of the lower thread 69 will result from a relation given by the formula:

$$f = F(1 - \sin\alpha), \tag{1}$$

where $\alpha$ is the angle established between the blade-shaped light beam 14 and the reference plane 49, and that between the pitch "F" and the necessary movement h of the bell 56 exists the following relation:

$$\text{(2) } NF = h/\sin\alpha \tag{2}$$

where N is the number of turns of the revolving unit 90 necessary to attain distance h.

In particular, it can be observed that the movement of the bell 98 is given by the formula:

$$NF - nf \tag{3}$$

that is, by considering the previous formulae (1) and (2), $$NF - nf = \frac{h}{\sin\alpha} - \frac{h}{\sin\alpha}(1 - \sin\alpha) \tag{4}$$

whereby developing the previous formula one obtains:

$$NF - nf = \frac{h}{\sin\alpha}(1 - 1 + \sin\alpha)$$

and by reducing the expression between the brackets the hereunder formula is attained:

$$NF - nf = \frac{h \sin\alpha}{\sin\alpha} = h. \tag{5}$$

Formula 5 indicates that for a preselected number of turns N of the revolving unit 56, having the disc brake 63 stopped, the bell 56 will move in respect to the reference plane 49 by a distance equal to h, while the distance c will change by a value equal to $h/\sin\alpha$. By a proper selection of the value of the angle $\alpha$, for example 30°, being $\sin 30° = \frac{1}{2}$, it results that when the bell 56 is moved by a distance h, the distance c will change by a value $h/\frac{1}{2} = 2h$ and the ratio between the pitches f and F 126 and 128 respectively becomes:

$$f = F(1 \sin 30°) = F(1 - \frac{1}{2}),$$
$$f = \frac{1}{2}F$$

This formula means that the pitch f will be just one half of the pitch F.

This system for moving the two sleeves 61 and 62 axially can be replaced by other means, such as for example, a mechanism comprising gear wheels and racks having different pitches, or by two threads having a similar pitch and actuated by two different movements imparting different turn members to each one, etc. For this purpose mechanisms having computer controlled stepping electric motors can be used in order to automate the fitting of the blade-shaped beam 14 to the dimensions of insert 10. Such mechanisms are known in the prior art and operate for the same purpose as the above disclosed coaxial sleeve system.

The practices of this invention can be readily modified to be particularly adaptable to detect dimensional changes of various articles of manufacture. A specific object is to provide an improved method and apparatus which also determines dimensional changes and provides automatic grading based on dimensional changes and defects. In one embodiment where the article is an insert having two plane and parallel surfaces, the insert edge surface or height is exposed to a pair of oppositely and angularly directed blade-shaped laser beams. The reflection of these beams are directed into an electro optical detector group for processing both edge defects and dimensional tolerances.

Figure 8:
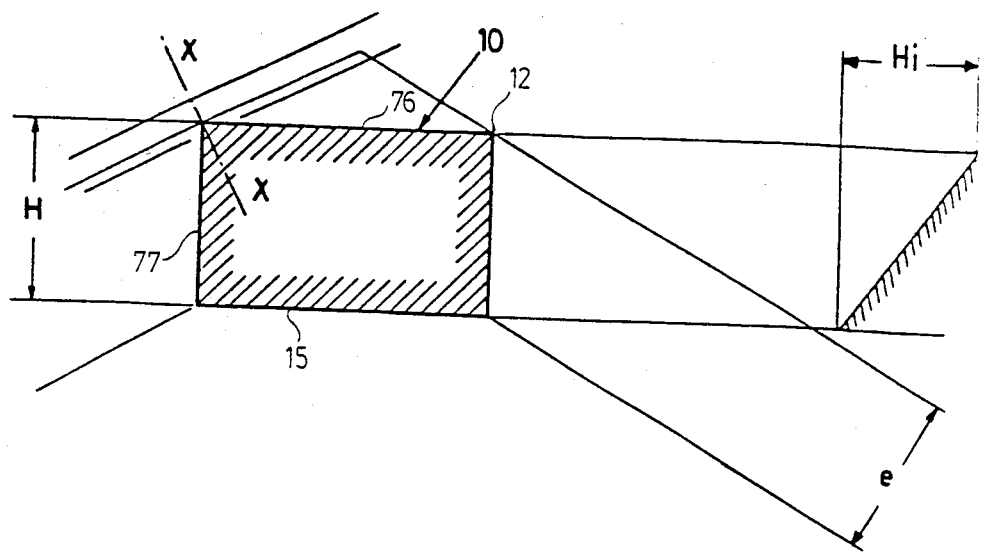
FIG. 8 is a schematic illustration of the laser beam principle of this invention for improved definition of dimensional changes.
Figure 9:
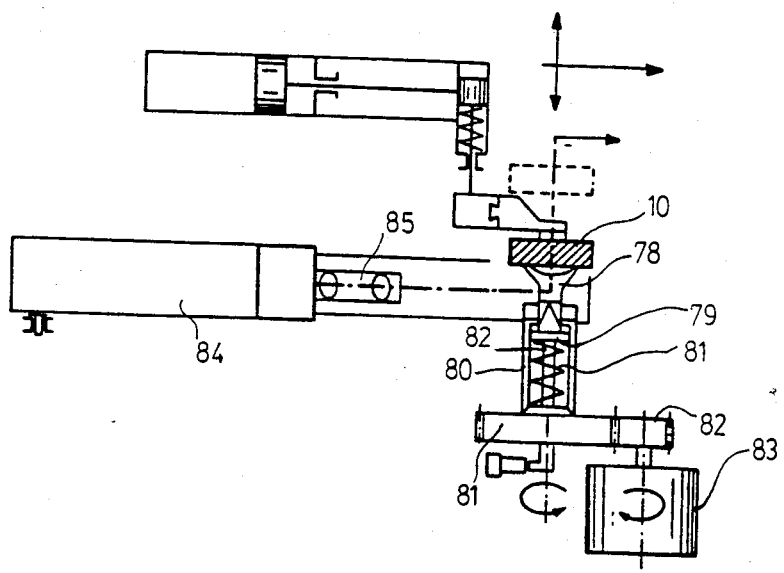
FIG. 9 is a schematic representation of an improved system for measuring dimensional changes.

Referring to FIG. 8, a metal insert 10 of FIG. 1, with a cutting edge 12 is defined by surfaces 75 and 76, and an edge or side surface 77 with a height H. Referring now to FIG. 9, insert 10 is placed on a suction cup 78 mounted to a sliding piston 79. Piston 79 in cylinder 80 is stressed to maximum extension by a compression spring 81 mounted co-axially around stem 82 of piston 79. The lower part of cylinder 80 is connected to a first gear-wheel 81, in mesh with a second gearwheel 82 which is controlled by a step by step motor shaft 83. Insert 10 on cup 78 is therefore caused to rotate in front of the laser beam source 84 which is connected a collimator 85, which in turn forms the beam to a blade-shape with a constant and minimal thickness.

Figure 10:
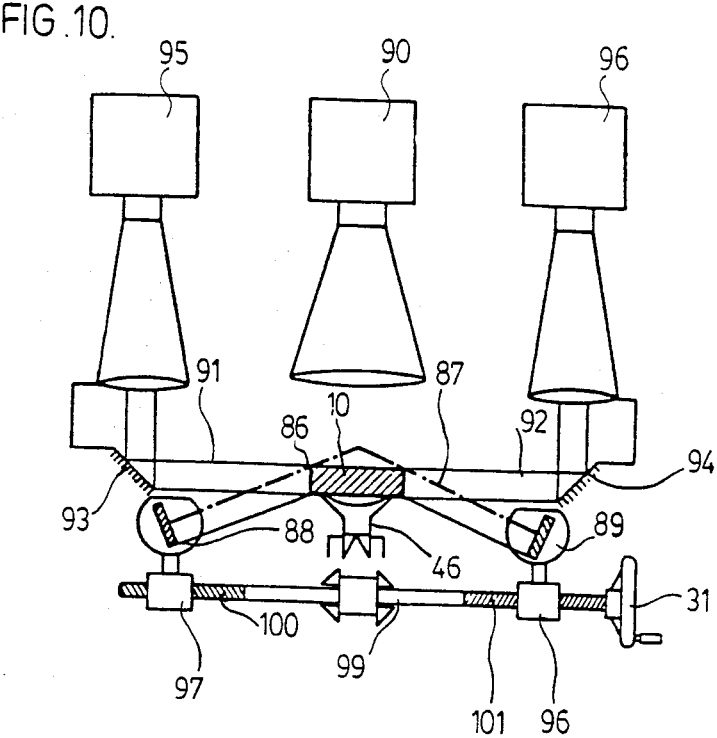
FIG. 10 is a schematic representation of a laser beam and TV camera apparatus for the practices of this invention.

With reference to FIG. 10 therefore, we can see that insert 10 is subjected to two diametrically opposite angularly directed laser beams 86 and 87 from sources 88 and 89. The laser beam sources 88 and 89 are positioned in such a way that the blade beams 86 and 87 strike the edge surface or sides of insert 10, and in particular upper edge 12. The angle is such that if there is any irregularity or chipping on the edges 12, the beams are diffracted and detected by TV camera 90 which is concentrically positioned with respect to said support and the beams, but for their refraction would converge between the camera and the insert. Camera 90 is also able to determine the angle position of these irregularities through a system of polar coordinates connected to the profile of the upper surface of insert 10.

Inspection of the opposite surfaces is made by turning or rotating the insert. The beams 86 and 87 which strike the side of insert 10 also generate the reflected beams 91 and 92 which by means of mirrors 93 and 94 are detected by a linear camera 95 and 96. In FIG. 10 two symmetrical linear TV cameras 95 and 96, and two reflecting mirrors 93 and 94 are shown.

It is evident that the image revealed by each TV camera 95 and 96 is transferred to a height of insert 10. This height is detected point by point in the course of the insert's rotation in front of the laser beams and is compared to a theoretical value previously recorded in an electronic memory and comparator. The memory and comparator directly compares (through the use of a microprocessor) the detected values with the theoretical parameters, and consequently grades the insert according to the results of the comparison.

To this end, it is necessary to define an optic plane of reference, with respect to which the insert is positioned and measured. As shown in FIG. 10, once insert 10 is positioned on support 46, it is rotated by the step motor 60 at 360°. Only the angle between 90° and 270° is used for the measurement function, while the first and last 90° of rotation are used for the acceleration and deceleration and rest of the support. The rotation between 90° and 270° is carried out at a constant angular velocity. It is clear that by increasing the number of laser sources, for example 4 symmetrical locations, the angle of measurement is reduced to >0° and therefore the capacity of the apparatus is increased.

It is important to stress that the laser beams 86 and 87 must be rigorously parallel rays from parallel and perpendicular sources so that when rotating the insert (since this is not usually circular in shape), the dimensions transmitted by mirrors 93 and 94 to TV camera 95 and 96 represents the real dimension of the side of insert 10. It is also important that the position or sources 93 and 94 of the laser beam must be adjustable with respect to the rotation axis of insert 10.

FIG. 10 illustrates a solution where the two laser beam sources 93 and 94 are mounted on sleeves 97 and 98, which are internally threaded and fixed on a shaft 99 with two parts 100 and 101 oppositely threaded. Rotation of handwheel 102 will provoke the equal and simultaneous approach or moving away of the sleeves and, therefore, of the laser beam sources with respect to the rotation axis of the insert 10 support.

Figure 11:
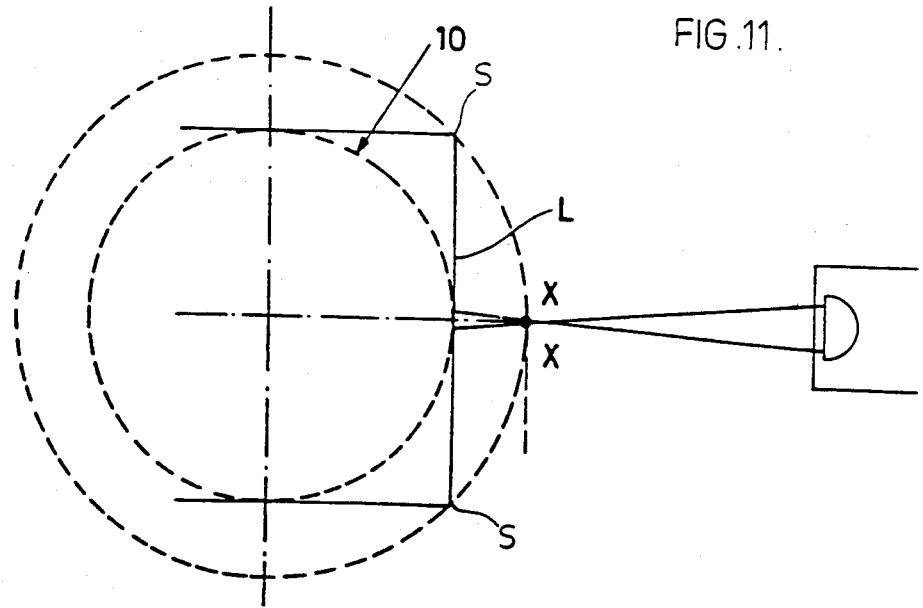
FIG. 11 is a schematic representation of the use of a blade-shaped laser beam similar to FIG. 7 above.

In FIG. 11, because of the slant of the converging laser beam along axis X—X, moving the beam perpendicularly to its diffusion direction causes the upper edge of insert 10 to be struck progressively by a beam concentrated in X—X, showing up the defects located by the edge itself. Since located defects are more harmful on the edges instead of on sides L, focal point X must coincide with the external diameter, i.e. the semidiagonal of insert 10, during the relative motion between the laser beam source and the insert.

Seen from above, the point X, i.e. the meeting point between axis X—X and the insert edge, provides the real coordinates of the profile of the upper surface plane, while the image diverted on lateral mirror 94 provides the real dimensions of the vertical plane.

It is obvious that with at least one output of laser beams 86 placed on a slant with respect to the position plane of insert 10 and TV camera 90, and at least one TV camera 95 it is possible:

(a) to detect defects and irregularities of the cutting edge;

(b) to detect or survey the dimensions of the insert, both of the upper surface profile, and the parallelism of the two delimiting surfaces of the insert.

At this point the information detected by TV cameras 90, 95 and 96, together with the detection of power supply frequency of the step motor 60, constitutes the real information for the computer system which may be programmed for the following:

(a) search and location of chippings;

(b) dimension detection on 3 axes;

(c) checking programs for specifications with or without grading subprograms;

(d) recording on cassettes of statistical data of dimension control and chippings;

(e) display of images on the monitor; and (f) print-out of displayed images.

Although the present invention has been described with reference to the foregoing specification, many modifications, combinations and variations of the invention will be apparent to those skilled in the art in light of the above teachings. It is therefore understood that changes may be made to the particular embodiments of the invention which are within the full intended scope of the invention as defined by the following claims.

I claim:

1. An imaging system for dimensional inspection and edge defect detection of metal inserts for machining operations having a pair of parallel surfaces and a planar edge surface defining a cutting edge therewith comprising in combination:

(a) support means supporting an insert in a darkened environment;

(b) optical means to project a single blade shaped light beam angularly across said insert cutting edge, said beam having a minimum width and corresponding maximum intensity at an area coincident with said cutting edge;

(c) said optical means includes a laser light source and a lens arrangement to provide a single triangular shaped beam which coverges in the direction of the insert so that the apex of the beam falls essentially on a point on said cutting edge;

(d) said optical means including a revolving head and revolving means therefor to move said light beam along said cutting edge said insert so that edge defects become a source of perturbations of the single blade shaped beam to provide light scattering and diffusion; and (e) electronic detection means to record and display said light scattering as a measurement of said defect or a dimensional change of said insert.

2. The invention as recited in claim 1 wherein said electronic detection means is an imaging system which creates an enlarged image of said insert based on said light scattering or diffusing and a computer means to provide dimensional inspection, defect counting and insert classification.

3. An imaging system according to claim 1 wherein said optical means includes a revolving head which is equipped with a plurality of mirrors positioned to make said single blade-shaped beam impinge against a cutting edge of an insert with a given inclination angle corresponding to an angle between said blade-shaped beam and a supporting plane of said insert, said mirrors transforming said light beam into the blade-shaped beam impinging against the said cutting edge of the insert, through two reflections having angles which are respectively, the first being the sum of 90° and the inclination angle of the blad-shaped beam in respect to said supporting plane of the insert and the second being the double of said inclination angle.

4. An imaging system according to claim 3 characterized in that the inclination angle between the said blade-shaped beam and said supporting plane is selected equal to 30° in a manner that the reflection angles of the said two mirrors are 120° and 60° respectively.

5. The invention as recited in claim 1 wherein said revolving head and revolving means therefor includes a mirror system to direct said light beam at a slight angle of incidence along peripheral cutting edges of said insert, said head being co-axially spaced from said insert and axially adjustable thereto.

6. An imaging system according to claim 5 wherein said optical means includes a focusing system comprising a lens system, the distance between said lens system and the cutting edge of the insert fixed, in a manner so that, when a polygon insert is being inspected, the distance between the periphery of the insert and revolving head will change in a given value in one direction while the distance between the lens system and the revolving head will change in an equal value in the opposite direction.

7. An imaging system according to claim 6 characterized in that the distance between the lens system and the said revolving head and the distance between said revolving head and the said supporting plane are changed in such a manner that a change in "h", the axial distance between the revolving head and the supporting plane, will correspond a change "h/sinα" of the distance between the lens system and revolving head, wherein "α" is the inclination angle of the blade-shaped ray in respect to the supporting plane.

8. An imaging system of claim 6 characterized in that an angle "α", the inclination angle of the blade-shaped ray in respect to the supporting plane, is selected equal to 30° in such a manner that a change in "h", the distance between revolving head and the insert supporting plane, will correspond a change "h" of the distance between revolving head and the insert supporting plane will correspond a change "2h" between the system and revolving head.

9. An imaging system according to claim 6 wherein a hollow sleeve incorporates the lens system and is equipped with two threads having respectively opposite directions and different pitches, one of said threads engaging a complementary thread supporting said rotary head and the other of said threads engaging a complementary thread on a co-axial sleeve so that rotation of said co-axial sleeve moves the lens system in one direction and the head to an opposite direction, so that indicating by "f" the pitch of the thread allowing the movement of the optical group and by "F" the pitch of the thread allowing the motion of the revolving head the ratio between said pitches is defined by the formula:

$$f = F(1 - \sin\alpha)$$

wherein angle "α" is the inclination angle of the blade-shaped ray in respect to the supporting palne.

10. An imaging system according to claim 6 characterized in that said distance changes are provided by two racks having tooth pitch ratio equal to the pitch ratio of the threads of claim 9.

11. An imaging system according to claim 6 characterized in that the two distance changes are provided by two stepping motors, having revolution ratio equal to the one mentioned in said claim 9.

12. An imaging system according to claim 6 wherein a hollow sleeve incorporates the lens system and is equipped with two threads having respectively opposite directions and different pitches, one of said threads engaging a complementary thread supporting said rotary head and the other of said threads engaging a complementary thread on a co-axial sleeve so that rotation of said co-axial sleeve moves the lens system in one direction and the head to an opposite direction, so that indicating by "f" the pitch of the thread allowing the movement of the optical group and by "F" the pitch of the thread allowing the motion of the revolving head and wherein an angle "α", the inclination angle in the blade-shaped ray in respect to the supporting plane, is made equal to 30° so that the ratio among the pitches of the threads and/or among the distance changes will result $f = \frac{1}{2}F$.

13. An imaging system for dimensional inspection and edge defect detection of a polygon-shaped body having a pair of parallel opposed surface and edge surfaces comprising:

(a) rotary support plane means adapted to support the polygon-shaped body having a pair of parallel opposed surfaces and edge surfaces, with one parallel surface resting on said support plane;

(b) a pair of leaser beam means laterally disposed from said support plane and at an oblique angle thereto, said laser beam means providing triangular shaped beams directed at an inclined angle to opposite edge surfaces so that the apex of each said beam is substantially coincident with a separate edge of the edge surface to which it is directed; and the two beams converge concentrically over one of said parallel surfaces;

(c) said beams being refracted by opposed edge surfaces and being oppositely and perpendicularly reflected by said opposed edge surfaces;

(d) means to rotate said rotary support so that reflections and refractions occur around the periphery of said body; and (e) an electro optical group adapted to receive said reflections and refractions and to thereby identify defects and dimensional changes.

14. The invention as recited in claim 13 wherein said electro optic group comprises a plurality of TV cameras which provide an enlarged image of said insert.

15. The invention as recited in claim 13 wherein said electro optical group includes three T.V. cameras, one of which is positioned coaxial with said insert to receive refractions of said beams which converge between said insert and said camera, and the other two cameras are aligned one each with said oppositely and laterally disposed laser sources to receive perpendicular reflections from the edge surfaces.

* * * * *